United States Patent [19]

Varma

[11] 4,265,815
[45] May 5, 1981

[54] 17-(SUBSTITUTED THIO)ANDROST-4-ENE[16,17,-b]-[1,4]BENZODIOXIN-3-ONES

[75] Inventor: Ravi K. Varma, Belle Mead, N.J.

[73] Assignee: E. R. Squibb & Sons, Inc., Princeton, N.J.

[21] Appl. No.: 135,823

[22] Filed: Mar. 31, 1980

[51] Int. Cl.³ .............................................. C07J 1/00
[52] U.S. Cl. ..................... 260/239.55 R; 260/397.45; 260/397.3
[58] Field of Search ................... 260/397.45, 239.55 R

[56] References Cited
U.S. PATENT DOCUMENTS

| | | | |
|---|---|---|---|
| 3,994,935 | 11/1976 | Varma et al. | 260/397.3 |
| 4,018,774 | 4/1977 | Varma et al. | 260/239.55 R |
| 4,091,036 | 5/1978 | Varma | 260/397.45 |
| 4,094,840 | 6/1978 | Varma | 260/239.55 R |
| 4,146,538 | 3/1979 | Varma et al. | 260/239.55 R |
| 4,164,504 | 8/1979 | Varma | 260/397.1 |

Primary Examiner—Elbert L. Roberts
Attorney, Agent, or Firm—Lawrence S. Levinson; Donald J. Barrack

[57] ABSTRACT

Steroids having the formula

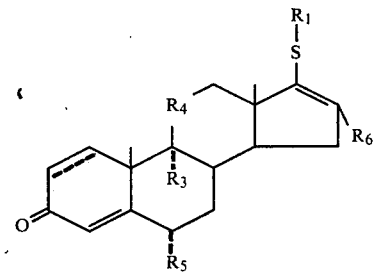

are useful intermediates for the preparation of novel antiinflammatory agents having the formula

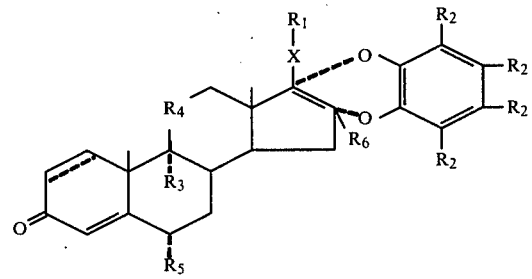

In the above formulas,
X is S,

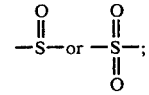

$R_1$ is alkyl, aryl, arylalkyl or acyloxyalkyl;
$R_2$ is fluoro, chloro, bromo or iodo (all $R_2$ groups are the same);
$R_3$ is hydrogen, fluoro, chloro, bromo or iodo;
$R_4$ is carbonyl, or $\beta$-hydroxymethylene;
$R_5$ is hydrogen, methyl or fluorine; and
$R_6$ is chloro, bromo, alkoxy, aryloxy, alkylthio, or arylthio.

10 Claims, No Drawings

17-(SUBSTITUTED THIO)ANDROST-4-ENE[16,17,-b]-[1,4]BENZODI-OXIN-3-ONES

BRIEF DESCRIPTION OF THE INVENTION

Steroids having the formula

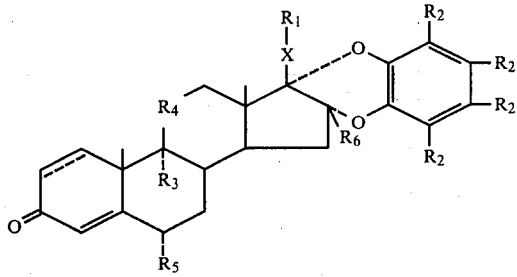

are disclosed herein and can be used as antiinflammatory agents. Also disclosed herein are novel intermediates for preparing the steroids of formula I; i.e., novel steroids having the formula

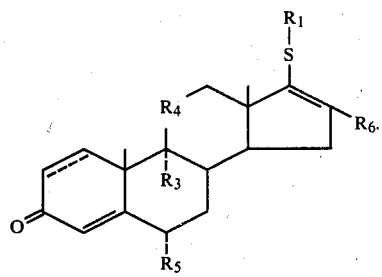

In formulas I and II, and throughout the specification the symbols are as defined below:

X is S,

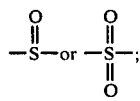

$R_1$ is alkyl, aryl, arylalkyl or acyloxyalkyl;
$R_2$ is fluoro, chloro, bromo or iodo (all $R_2$ groups are the same);
$R_3$ is hydrogen, fluoro, chloro, bromo or iodo;
$R_4$ is carbonyl, or $\beta$-hydroxymethylene;
$R_5$ is hydrogen, methyl or fluorine; and
$R_6$ is chloro, bromo, alkoxy, aryloxy, alkylthio, or arylthio.

A dotted line in the 1,2-position of a structural formula in this disclosure indicates the optional presence of ethylenic unsaturation.

The term "aryl", as used throughout the specification, whether by itself or as part of a larger group, refers to phenyl or phenyl substituted with one or two alkyl, alkoxy or halo groups.

The term "halo", as used throughout the specification, whether by itself or as part of a larger group, refers to fluoro, chloro, bromo or iodo.

The terms "alkyl" and "alkoxy", as used throughout the specification, either individually or as part of a larger group, refer to groups having 1 to 10 carbon atoms.

The term "acyloxy", as used throughout the specification, whether by itself or as part of a larger group, refers to a group having the formula

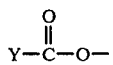

wherein Y is alkyl or aryl.

DETAILED DESCRIPTION OF THE INVENTION

The steroids of formula I are physiologically active substances that possess glucocorticoid and antiinflammatory activity. They can be used topically in the treatment of skin conditions such as dermatitis, sunburn, neurodermatitis, eczema, and anogenital pruritus. The steroids of formula I can be used in the range of 0.01 to 5.0% by weight, preferably 0.05 to 2.0% by weight in a conventional cream or lotion.

The steroids of formula II are novel intermediates that are useful for the preparation of the topically active antiinflammatory steroids of formula I; as such, they form an integral part of this invention.

The steroids of formula II can be prepared from the corresponding $\Delta^{4,16}$-steroid having the formula

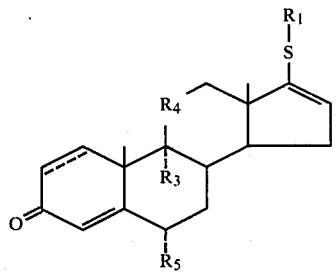

The $\Delta^{4,16}$-androstenes of formula III are known in the art; see, for example, U.S. Pat. Nos. 4,091,036, 4,094,840, 4,133,811, and 4,146,538. As disclosed therein, reaction of the appropriate androsten-17-one with a thiol compound having the formula

  (IV)

in the presence of a Lewis acid (e.g., boron trifluoride etherate), yields an intermediate having the formula

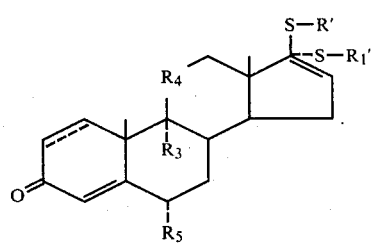

In formulas IV and V, and throughout the specification, $R'_1$ is alkyl, aryl or arylalkyl. The reaction can be run in an organic solvent (e.g., a halogenated hydrocarbon), or a mixture of organic solvents. The use of some glacial acetic acid improves yields. Reaction conditions are not critical and the reaction can be conveniently run at room temperature, preferably in an inert atmosphere (e.g., argon or nitrogen). Better yields may be obtained with relatively short reaction times (less than 1 hour).

An androstene of formula V can be converted to the corresponding steroid having the formula

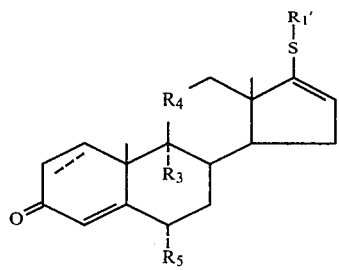

VI by simply heating the steroid in an inert solvent (e.g., diethylbenzene or dichlorobenzene).

Those steroids of formula III wherein $R_1$ is acyloxyalkyl can be prepared by first oxidizing a steroid of formula VI, wherein $R'_1$ is alkyl, using one equivalent of oxidizing agent, to obtain a steroid having the formula

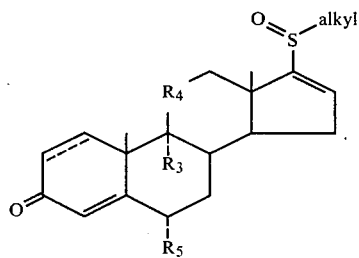

VII

A 17-alkylsulfinyl steroid of formula VII can be reacted with an appropriate acid anhydride, and a basic catalyst such as the sodium salt of the corresponding acid, to yield the corresponding 17-[[(acyloxy)alkyl]thio]steroid having the formula

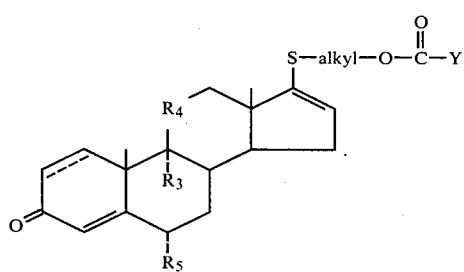

VIII

The intermediates of formula II wherein $R_6$ is chloro or bromo can be obtained by reacting a steroid of formula III with N-halosuccinimide, preferably in a halogenated hydrocarbon solvent.

The intermediates of formula II wherein $R_6$ is alkoxy or aryloxy can be obtained by reacting a steroid of formula II wherein $R_6$ is chloro or bromo with an alkali metal alkoxide or an alkali metal aryloxide, preferably in an alkanol solvent.

The intermediates of formula II wherein $R_6$ is alkylthio or arylthio can be obtained by reacting a steroid of formula III with an alkyl or aryl sulfenyl halide, preferably in a halogenated hydrocarbon solvent.

Reaction of an intermediate of formula II with an o-benzoquinone having the formula

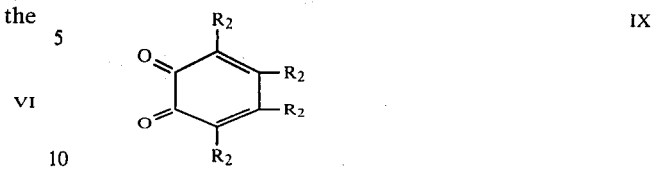

IX yields a product of formula I, wherein X is sulfur; i.e., a steroid having the formula

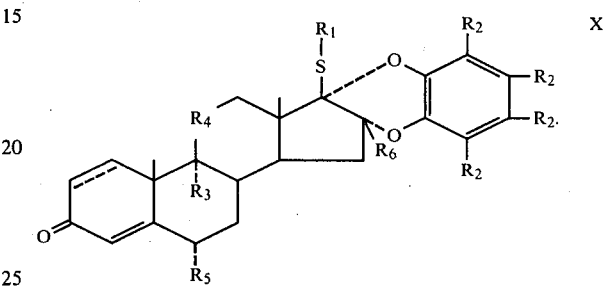

X

The reaction proceeds at room temperature.

Oxidation of an androstene of formula X with a peracid (e.g., m-chloroperbenzoic acid), a peracid salt (e.g., sodium m-periodate) or a peroxide (e.g., hydrogen peroxide) yields the corresponding sulfinyl product having the formula

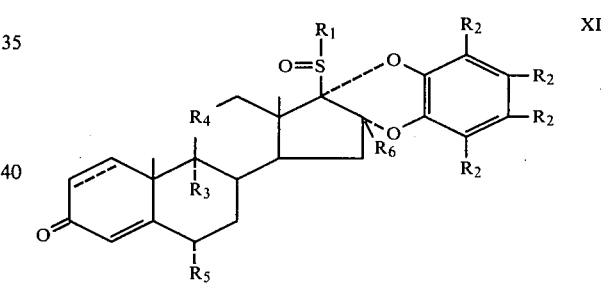

XI or the corresponding sulfonyl product having the formula

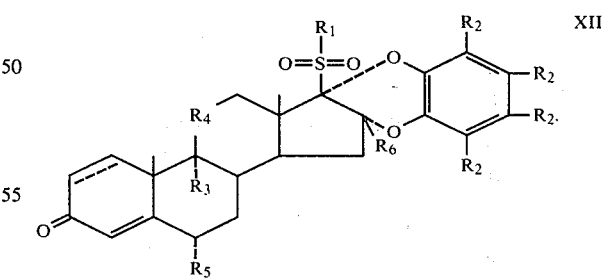

XII

The use of one equivalent of oxidizing agent will yield predominantly the sulfinyl derivative of formula XI and the use of two or more equivalents of oxidizing agent will yield predominantly the sulfonyl derivative of formula XII.

Many alternative processes for the preparation of the steroids of this invention are available. For example, the sulfinyl and sulfonyl products of formulas XI and XII (wherein $R_6$ is other than chloro or bromo) can be prepared by oxidizing an intermediate of formula II to obtain novel intermediates having the formulas

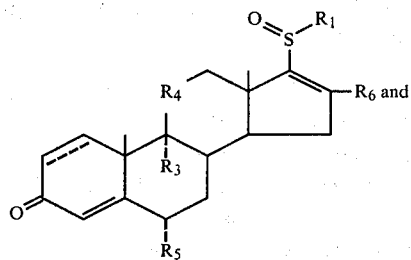

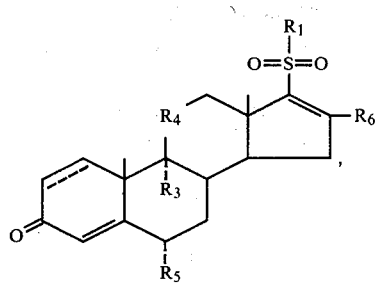

which can in turn be reacted with an o-benzoquinone of formula IX. Intermediates of formulas XIII and XIV wherein $R_6$ is chloro or bromo will not react with an o-benzoquinone of formula IX. They are useful as intermediates, however, because the 16-halo group can be displaced with an alkoxy, aryloxy, alkylthio, or arylthio group to give intermediates which will react with an o-benzoquinone of formula IX.

Those steroids of formula I wherein $R_4$ is β-hydroxymethylene are preferred. Also preferred are those steroids of formula I wherein $R_3$ is fluoro. Also preferred are those steroids of formula I wherein $R_2$ is chloro. Most preferred are those steroids having the structural formula

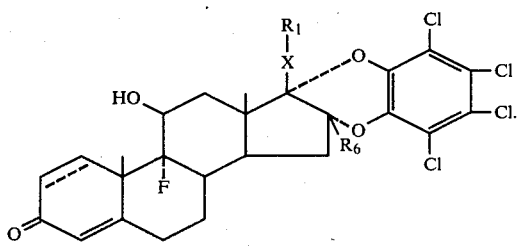

The following examples are specific embodiments of this invention.

EXAMPLE 1

(11β,16β,17)-5′,6′,7′,8′,16-Pentachloro-17-(ethylthio)-9-fluoro-2′,3′-dihydro-11-hydroxyandrosta-1,4-dieno[16,17-b][1,4]benzodioxin-3-one (A)

(11β)-16-Chloro-17-(ethylthio)-9-fluoro-11-hydroxyandrosta-1,4,16-trien-3-one

A solution of 1.5 g of 17-(ethylthio)-9-fluoro-11β-hydroxyandrosta-1,4,16-trien-3-one in 70 ml of dry dichloromethane is stirred with 609 mg of N-chlorosuccinimide at room temperature under a nitrogen atmosphere for 2.5 hours. The resulting solution is diluted with 140 ml of chloroform; the chloroform solution is washed with saturated $NaHCO_3$ solution and water, dried over anhydrous $Na_2SO_4$ and evaporated in vacuo to give 1.65 g of a foam. The foam is dissolved in chloroform-hexane (4:1) and chromatographed on a 60 g-silica gel column. Elution with chloroform-hexane (4:1) gives 1.2 g of a tlc-homogenous material. Crystallization from acetone-hexane gives 815 mg of an analytical specimen of the title compound, melting point 240°–241° C. (dec).

Anal. calc'd for $C_{21}H_{26}ClFO_2S$: C,63.54; H,6.60; Cl,8.93; F,4.79; S,8.08. Found: C,63.42; H,6.37; Cl,8.84; F,5.02; S,8.23.

(B)

(11β,16β,17)-5′,6′,7′,8′,16-Pentachloro-17-(ethylthio)-9-fluoro-2′,3′-dihydro-11-hydroxyandrosta-1,4-dieno[16,17-b][1,4]benzodioxin-3-one A solution of 397 mg of (11β)-16-chloro-17-(ethylthio)-9-fluoro-11-hydroxyandrosta-1,4,16-trien-3-one and 270 mg of tetrachloro-o-benzoquinone in 10 ml of dry tetrahydrofuran is stirred at room temperature under a nitrogen atmosphere for 65 hours. More tetrachloro-o-benzoquinone is added and stirring is continued for 24 hours. A few drops of water are added to the resulting solution and the solvent is evaporated in vacuo to give a gummy material. This is dissolved in chloroform and quickly eluted through a 15 g-silica gel column with 500 ml of chloroform. The chloroform is removed in vacuo to give 510 mg of a foam which is redissolved in chloroform-hexane (4:1) and chromatographed on a 20 g-silica gel column. Elution with chloroform-hexane (4:1) gives 430 mg of a homogeneous title compound. Crystallization from ethyl acetate-hexane gives 310 mg of an analytical specimen, melting point 255°–256° C. (dec).

Anal. calc'd for $C_{27}H_{26}Cl_5FO_4S$: C,50.44; H,4.08; Cl,27.58; F,2.96; S,4.99. Found: C,50.75; H,4.17; Cl,27.40; F,2.99; S,4.90.

EXAMPLE 2

(11β,16β,17)-5′,6′,7′,8′-Tetrachloro-17-(methylthio)-16-[(4-methylphenyl)thio]-9-fluoro-2′,3′-dihydro-11-hydroxyandrosta-1,4-dieno[16,17-b][1,4]benzodioxin-3-one (A)

(11β)-9-Fluoro-11-hydroxy-16-[(4-methylphenyl)thio]-17-(methylthio)androsta-1,4,16-trien-3-one A solution of 900 mg of 9-fluoro-11β-hydroxy-17-(methylthio)androsta-1,4,16-trien-3-one in 900 ml of dichloromethane is stirred with 500 mg of p-toluenesulfenyl chloride at room temperature under a nitrogen atmosphere for about 16 hours. The resulting solution is washed with water, dried over anhydrous $Na_2SO_4$ and evaporated in vacuo to give 1.3 g of a solid, which is dissolved in chloroform-hexane (3:2) and chromatographed on a 50 g-silica gel column. Elution with chloroform-hexane (3:2) gives 930 mg of a tlc-homogenous material. Two crystallizations from acetone-hexane give 400 mg of an analytical specimen of the title compound, melting point 205°–206° C.

Anal. calc'd for $C_{27}H_{31}FO_2S_2$: C,68.90; H,6.64; F,4.04; S,13.64. Found: C,69.14; H,6.53; F,4.10; S,13.50.

(B)
(11β,16β,17)-5',6',7',8'-Tetrachloro-17-(methylthio)-16-[(4-methylphenyl)thio]-9-fluoro-2',3'-dihydro-11-hydroxyandrosta-1,4-dieno[16,17-b]-[1,4]benzodioxin-3-one A solution of (11β)-9-fluoro-11-hydroxy-16-[(4-methylphenyl)thio]-17-(methylthio)androsta-1,4,16-trien-3-one (650 mg) in dry tetrahydrofuran (15 ml) is mixed with a solution of tetrachloro-o-benzoquinone (480 mg) in dry tetrahydrofuran (15 ml) and after about 1½ days the solution is evaporated to dryness. The residue is dissolved in chloroform-hexane (7:3) and chromatographed on a silica gel column (65 g) eluting with chloroformhexane mixtures and chloroform to isolate the title compound. This material is further purified by preparative thin layer chromatography on silica gel plates using chloroform-ethyl acetate (9:1) for development. The title compound (650 mg) is isolated and crystallized from ether-hexane to give 440 mg of the title compound, melting point 198°–201° C.

Anal. calc'd for $C_{33}H_{31}Cl_4FO_4S_2$: C,55.31; H,4.36; Cl,19.79; F,2.65; S,8.95. Found: C,55.18; H,4.27; Cl,19.71; F,2.59; S,8.73.

EXAMPLE 3

(11β,16β,17β)-5=,6',7',8'-Tetrachloro-17-(ethylsulfonyl)-9-fluoro-2',3'-dihydro-11-hydroxy-16-methoxyandrosta-1,4-dieno[16,17-b][1,4]benzodioxin-3-one (A)
(11β)-16-Chloro-17-(ethylsulfonyl)-9-fluoro-11-hydroxyandrosta-1,4,16-trien-3-one To a solution of (11β)-16-chloro-17-(ethylthio)-9-fluoro-11-hydroxyandrosta-1,4,16-trien-3-one (200 mg; see Example 1A) in dichloromethane (20 ml) is added a solution of 85% m-chloroperoxybenzoic acid (205 mg) in dichloromethane (20 ml). After 1 hour the solution is washed with a dilute sodium carbonate solution and water, dried (anhydrous $MgSO_4$) and evaporated to yield 200 mg of the title compound.

(B)
(11β)-17-(Ethylsulfonyl)-16-methoxy-9-fluoro-11-hydroxyandrosta-1,4,16-trien-3-one A suspension of (11β)-16-chloro-17-(ethylsulfonyl)-9-fluoro-11-hydroxyandrosta-1,4,16-trien-3-one (1.29 g; prepared as described above) in anhydrous methanol (190 ml) containing sodium methoxide (800 mg) is refluxed for 3 hours. The resulting solution is concentrated in vacuo, diluted with water, saturated with sodium chloride and extracted with ethyl acetate. The ethyl acetate extract is washed with water, dried (anhydrous $Na_2SO_4$) and evaporated to afford the crude material (1.2 g). This is chromatographed over silica gel (60 g) to isolate the title compound (505 mg), melting point 288°–289° C., after crystallization from acetone-hexane.

(C)
(11β,16β,17β)-5',6',7',8'-Tetrachloro-17-(ethylsulfonyl)-9-fluoro-2',3'-dihydro-11-hydroxy-16-methoxyandrosta-1,4-dieno[16,17-b]-[1,4]benzodioxin-3-one A solution of (11β)-17-(ethylsulfonyl)-16-methoxy-9-fluoro-11-hydroxyandrosta-1,4,16-trien-3-one (500 mg) in dry tetrahydrofuran (15 ml) is mixed with a solution of tetrachloro-o-benzoquinone (318 mg) in dry tetrahydrofuran at room temperature. After 24 hours, another portion of tetrachloro-o-benzoquinone (318 mg) dissolved in dry tetrahydrofuran (10 ml) is added. After another 24 hours the solvent is evaporated in vacuo, and the residual solid is washed several times with chloroform-hexane to afford the title compound (650 mg), melting point 194°–197° C.

EXAMPLE 4

(11β,16β,17β)-5',6',7',8'-Tetrabromo-16-chloro-9-fluoro-2',3'-dihydro-11-hydroxy-17-(methylthio)androsta-1,4-dieno[16,17-b][1,4]benzodioxin-3-one (A)
(11β)-16-Chloro-9-fluoro-11-hydroxy-17-(methylthio)androsta-1,4,16-trien-3-one To a solution of 9-fluoro-11β-hydroxy-17-(methylthio)androsta-1,4,16-trien-3-one (100 mg) in a mixture of dry dichloromethane (10 ml) and methanol (8 ml) is added a 0.31 molar solution of chlorine in dichloromethane (1.0 ml). After a few hours, the solution is poured into a dilute sodium bicarbonate solution. The product is isolated by extraction with chloroform and the chloroform solution is washed with water, dried (anhydrous $MgSO_4$) evaporated and the residue is purified by preparative thin layer chromatography to afford the title compound (35 mg), melting point 262°–268° C.

(B)
(11β,16β,17β)-5',6',7',8'-Tetrabromo-16-chloro-9-fluoro-2',3'-dihydro-11-hydroxy-17-(methylthio)androsta-1,4-dieno[16,17-b][1,4]benzodioxin-3-one Following the procedure of Example 1B, but substituting (11β)-16-chloro-9-fluoro-11-hydroxy-17-(methylthio)androsta-1,4,16-trien-3-one for (11β)-16-chloro-17-(ethylthio)-9-fluoro-11-hydroxyandrosta-1,4,16-trien-3-one and tetrabromo-o-benzoquinone for tetrachloro-o-benzoquinone yields the title compound.

EXAMPLE 5

(11β,16β,17β)-5',6',7',8',16-Pentabromo-17-(ethylthio)-9-fluoro-2',3'-dihydro-11-hydroxyandrosta-1,4-dieno[16,17-b][1,4]benzodioxin-3-one (A)
(11β)-16-Bromo-17-(ethylthio)-9-fluoro-11-hydroxyandrosta-1,4,16-trien-3-one A solution of (11β)-17-(ethylthio)-9-fluoro-11-hydroxyandrosta-1,4,16-trien-3-one (181 mg) in dichloromethane (10 ml) containing N-bromosuccinimide (98 mg) is stirred at room temperature for 2 hours and the reaction mixture is subjected to preparative thin layer chromatography on silica gel plates to isolate the title compound.

(B)
(11β,16β,17β)-5',6',7',8',16-Pentabromo-17-(ethylthio)-9-fluoro-2',3'-dihydro-11-hydroxyandrosta-1,4-dieno[16,17-b][1,4]benzodioxin-3-one Following the procedure of Example 1B, but substituting (11β)-16-bromo-17-(ethylthio)-9-fluoro-11-hydroxyandrosta-1,4,16-trien-3-one for (11β)-16-chloro-17-(ethylthio)-9-fluoro-11-hydroxyandrosta-1,4,16-trien-3-one and tetrabromo-o-benzoquinone for tetrachloro-o-benzoquinone, yields the title compound.

EXAMPLE 6

(11β,16β,17β)-17-(Ethylsulfinyl)-5',6',7',8',9-pentafluoro-2',3'-dihydro-11-hydroxy-16-(methylthio)androsta-1,4-dieno[16,17-b][1,4]benzodioxin-3-one

(A)

(11β)-16-Chloro-17-(ethylsulfinyl)-9-fluoro-11-hydroxyandrosta-1,4,16-trien-3-one To (11β)-16-chloro-17-(ethylthio)-9-fluoro-11-hydroxyandrosta-1,4,16-trien-3-one (100 mg; see Example 1A) in dichloromethane (15 ml) is added a solution of 85% m-chloroperbenzoic acid (56 mg) in dichloromethane (5.0 ml) over a period of 2 minutes. After 1 hour the solution is washed with a dilute sodium carbonate solution and water, dried (anhydrous MgSO₄) and evaporated to yield the title compound.

(B)

(11β)-17-(Ethylsulfinyl)-9-fluoro-11-hydroxy-16-(methylthio)androsta-1,4,16-trien-3-one A solution of (11β)-16-chloro-17-(ethylsulfinyl)-9-fluoro-11-hydroxyandrosta-1,4,16-trien-3-one (100 mg) in anhydrous methanol (12 ml) containing sodium methoxide (70 mg) and methanethiol (0.5 ml) is stirred under an atmosphere of nitrogen for 20 hours and then poured into water. The solution is extracted with ethyl acetate and the ethyl acetate solution is washed with water, dried (anhydrous MgSO₄) and evaporated to afford a solid (104 mg). This solid is subjected to chromatography on silica gel plates to isolate the title compound.

(C)

(11β,16β,17β)-17-(Ethylsulfinyl)-5',6',7',8',9-pentafluoro-2',3'-dihydro-11-hydroxy-16-(methylthio)androsta-1,4-dieno[16,17-b][1,4]-benzodioxin-3-one Following the procedure of Example 1B, but substituting (11β)-17-(ethylsulfinyl)-9-fluoro-11-hydroxy-16-(methylthio)androsta-1,4,16-trien-3-one for (11β)-16-chloro-17-(ethylthio)-9-fluoro-11-hydroxyandrosta-1,4,16-trien-3-one and tetrafluoro-o-benzoquinone for tetrachloro-o-benzoquinone, yields the title compound.

What is claimed is:

1. A steroid having the formula

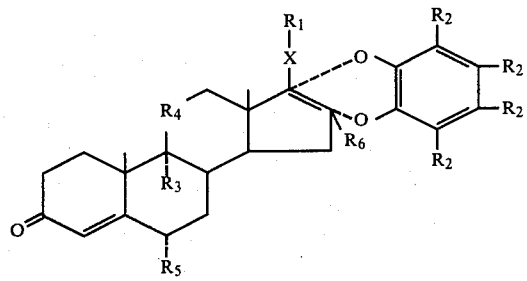

or the 1,2-dehydro derivative thereof, wherein X is S,

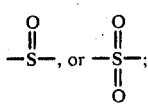

$R_1$ is alkyl, aryl, arylalkyl or acyloxyalkyl;

$R_2$ is fluoro, chloro, bromo or iodo (all $R_2$ groups are the same);

$R_3$ is hydrogen, fluoro, chloro, bromo or iodo;

$R_4$ is carbonyl, or β-hydroxymethylene;

$R_5$ is hydrogen, methyl or fluorine; and $R_6$ is chloro, bromo, alkoxy, aryloxy, alkylthio, or arylthio.

2. A steroid in accordance with claim 1 wherein $R_4$ is β-hydroxymethylene.

3. A steroid in accordance with claim 1 wherein $R_3$ is fluoro.

4. A steroid in accordance with claim 1 wherein $R_5$ is hydrogen.

5. A steroid in accordance with claim 1 wherein $R_2$ is chloro.

6. A steroid in accordance with claim 1 having the formula

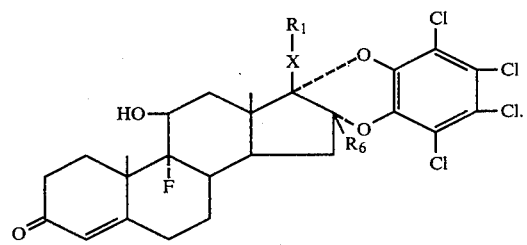

or the 1,2-dehydro derivative thereof.

7. A steroid in accordance with claim 6 wherein X is S.

8. A steroid in accordance with claim 6 wherein X is

9. A steroid in accordance with claim 6 wherein X is

10. A steroid having the formula

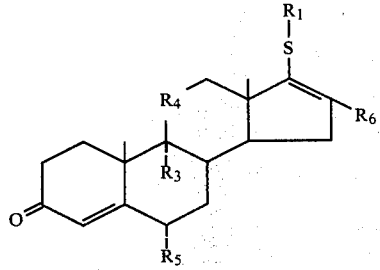

or the 1,2-dehydro derivative thereof, wherein
$R_1$ is alkyl, aryl, arylalkyl or acyloxyalkyl;
$R_3$ is hydrogen, fluoro, chloro, bromo or iodo;
$R_4$ is carbonyl, or β-hydroxymethylene;
$R_5$ is hydrogen, methyl or fluorine; and
$R_6$ is chloro, bromo, alkoxy, aryloxy, alkylthio, or arylthio.

* * * * *

UNITED STATES PATENT AND TRADEMARK OFFICE
CERTIFICATE OF CORRECTION

PATENT NO. : 4,265,815
DATED : May 5, 1981
INVENTOR(S) : Ravi K. Varma

It is certified that error appears in the above-identified patent and that said Letters Patent are hereby corrected as shown below:

In column 7, line 26, the first line of Example 3, after "5", delete "=" and add in its place --'--.

In the structural formula in claim 1, delete the second bond in the 16,17-position.

Signed and Sealed this

Eighth Day of December 1981

[SEAL]

*Attest:*

*Attesting Officer*

GERALD J. MOSSINGHOFF
*Commissioner of Patents and Trademarks*